United States Patent [19]

Satoh et al.

[11] Patent Number: 4,877,797
[45] Date of Patent: * Oct. 31, 1989

[54] 1,4-DIHYDROPYRIDINE DERIVATIVES AND PHARMACEUTICAL COMPOSITIONS CONTAINING SAME

[75] Inventors: Hiroaki Satoh, Saitama; Hiroyasu Koyama, Ageo; Yoshikuni Suzuki, Ohmiya; Toshiji Sugai; Koichi Watanabe, both of Saitama, all of Japan

[73] Assignee: Nisshin Flour Milling Co., Ltd., Tokyo, Japan

[*] Notice: The portion of the term of this patent subsequent to Jul. 12, 2005 has been disclaimed.

[21] Appl. No.: 67,719

[22] Filed: Jun. 15, 1987

[30] Foreign Application Priority Data

Jun. 13, 1986 [JP] Japan ................ 61-136152

[51] Int. Cl.[4] ............... A61K 31/44; C07D 401/12
[52] U.S. Cl. .................. 514/314; 514/290; 514/312; 514/332; 514/335; 546/156; 546/170; 546/110; 546/101; 546/263; 546/261
[58] Field of Search ............... 546/263, 156, 170, 110, 546/101, 263, 261; 514/332, 290, 312, 335

[56] References Cited

U.S. PATENT DOCUMENTS 3,862,161 1/1975 Bossert et al. ............ 546/256
4,497,808 2/1985 Zimmermann et al. ...... 546/256
4,656,181 4/1987 Sunkel et al. ............ 546/321
4,757,071 7/1988 Koyama et al. ............ 514/247

Primary Examiner—Jane T. Fan
Attorney, Agent, or Firm—Cushman, Darby & Cushman

[57] ABSTRACT

Compounds are described of the formula

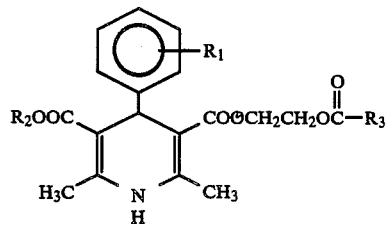

(I)

wherein $R_1$ is a nitro or trifluoromethyl group; $R_2$ is a $C_1$–$C_6$ alkyl group; $R_3$ is a pyridyl or pyridyl N-oxide group which may be substituted with halogen, hydroxyl, haloalkyl, $C_1$–$C_6$ alkoxy or $C_1$–$C_6$ alkyl and further may be fused with a benzene or naphthalene ring, said ring being optionally substituted with $C_1$–$C_6$ alkyl, $C_1$–$C_6$ alkoxy, halogen or haloalkyl, and a pharmaceutically acceptable acid addition salt thereof. The compounds of the formula (I) are of vasodilating and blood pressure lowering activities and thus may be useful for the treatment of cardiac diseases, cerebrovascular diseases and hypertension.

10 Claims, No Drawings

1,4-DIHYDROPYRIDINE DERIVATIVES AND PHARMACEUTICAL COMPOSITIONS CONTAINING SAME

FIELD OF THE INVENTION

The present invention relates to new compounds having valuable vasodilating and blood pressure lowering effects, etc., to processes for their preparation and to their use as vasodilating and antihypertensive agents.

BACKGROUND OF THE INVENTION 1,4-Dihydro-2,6-dimethyl-4-phenylpyridine-3,5-dicarboxylic acid diethyl ester is known to be obtained by reacting 2-benzylideneacetoacetic acid ethyl ester, β-aminocrotonic acid ethyl ester or acetoacetic acid ethyl ester and ammonia, as reported in Ber. Deutsch Chem. Ges. 31, 743(1971). DOS 2117517 and 2117573 disclose that similar compounds can be used as coronary arteriodilating and antihypertensive agents, and inter alia 1,4-dihydro-2,6-dimethyl-4-(2-nitrophenyl)-pyridine-3,5-dicarboxylic acid dimethyl ester disclosed therein has been used extensively under the name of Nifedipine. Since the commercial success of Nifedipine, a large number of compounds having a similar chemical structure have been developed and these compounds are disclosed in U.S. Pat. Nos. 3,574,843; 4,264,611; 3,799,934; 4,239,893; 4,317,768; 4,044,141 and 4,258,042; EPO Appln. 0012180; and French Pat. No. 2,182,983. Further, there are reported in WO 84/02132 the compounds wherein a heterocyclic group is linked to an alkylene group through an amide bond in an ester moiety at the 3-position of 1,4-dihydro-2,6-dimethyl-4-phenyl pyridine-3,5-dicarboxylic acid diesters. Known 1,4-dihydropyridine derivatives including Nifedipine inhibit calcium influx into the cells and they have been used as a remedy for cardiac diseases of angina pectoris, etc., cerebrovascular diseases of cerebral infarction, etc., and hypertension.

However, it has been reported that these derivatives have the disadvantages such as short-lasting activity and tachycardia.

The present invention results from efforts to develop new compounds with more improved pharmacological effects and lesser side effects than known 1,4-dihydropyridine derivatives.

DISCLOSURE OF THE INVENTION

According to the present invention, there are provided compounds of the formula I

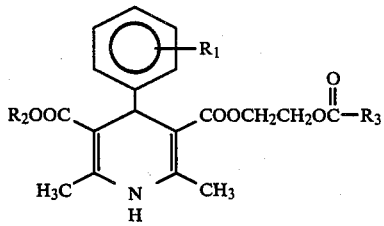

(I)

wherein $R_1$ is a nitro or trifluoromethyl group; $R_2$ is a $C_1$–$C_6$ alkyl group; $R_3$ is a pyridyl or pyridyl N-oxide group which may be substituted with halogen, hydroxyl, haloalkyl, $C_1$–$C_6$ alkoxy or $C_1$–$C_6$ alkyl and further may be fused with a benzene or naphthalene ring, said ring being optionally substituted with $C_1$–$C_6$ alkyl, $C_1$–$C_6$ alkoxy, halogen or haloalkyl, and a pharmaceutically acceptable acid addition salt thereof.

By the term "pharmaceutically acceptable acid addition salt" is meant a salt, the anion of which is relatively innocuous to the animal organism when used in therapeutic doses, so that the beneficial properties of the cation are not vitiated by side-effects ascribable to the anion.

In the present specification, wherever reference is made to compounds of formula I, it is intended to refer also to the said acid addition salts, where the context so permits.

As is evident from the above formula I, the compounds of the present invention are those wherein $R_3$ is linked to an alkylene group through an ester bond (carbonyloxy group), which are different from the compounds wherein the heterocyclic group is linked to an alkylene group through an amide bond in an ester moiety at 3-position of 1,4-dihydro-2,6-dimethyl-4-phenyl-pyridine-3,5-dicarboxylic acid diesters as disclosed in the above-cited prior art WO 84/02132. The compounds of the present invention are characterized by prominent pharmacological effects as compared with the prior art compounds.

Examples of suitable group for $R_1$ in the formula (I) include 2-trifluoromethyl, 3-trifluoromethyl, 2-nitro and 3-nitro.

Examples of suitable groups for $R_2$ include methyl, ethyl, n-propyl, i-propyl, n-butyl, i-butyl and tert.-butyl, and the like.

Examples of suitable groups for $R_3$ include pyridyl and pyridyl-N-oxide, e.g., 3-pyridyl, 4-pyridyl, 3-pyridyl-N-oxide and 4-pyridyl-N-oxide, and the like. Also, examples of suitable substituents on the pyridyl and pyridyl N-oxide groups include fluorine, chlorine and hydroxyl, and the like. One or more of the substituents may be present on the pyridyl and pyridyl N-oxide groups.

When the pyridyl or pyridyl N-oxide group is fused with a benzene or naphthalene ring to form a fused group, examples of suitable fused groups include 2-quinolyl, 3-quinolyl, 4-quinolyl and 3-(7,8-benzoquinolyl), and the like. When the benzene and naphthalene rings have substituents, examples of suitable substituents include methyl, ethyl, methoxy, ethoxy, fluorine, chlorine, trifluoromethyl and trichloromethyl, and the like. The number of these substituents may be one or more.

Examples of preferred compounds according to the invention are listed below.

1. 2,6-dimethyl-4-(2-trifluoromethylphenyl)-1,4-dihydropyridine-3,5-dicarboxylic acid 3-[2-(4-chloro-6-methyl-3-quinolinecarboxy)ethyl]ester-5-methyl ester
2. 2,6-dimethyl-4-(2-nitrophenyl)-1,4-dihydropyridine-3,5-dicarboxylic acid 3-[2-(3-(pyridine-1-oxide)carboxy)ethyl]ester-5-methyl ester
3. 2,6-dimethyl-4-(2-trifuloromethylphenyl)-1,4-dihydropyridine-3,5-dicarboxylic acid 3-[2-(3-(pyridine-1-oxide)carboxy)ethyl]ester-5-methyl ester
4. 2,6-dimethyl-4-(2-nitrophenyl)-1,4-dihydropyridine-3,5-dicarboxylic acid 3-[2-(4-hydroxy-8-methyl-3-quinolinecarboxy)ethyl]ester-5-methyl ester
5. 2,6-dimethyl-4-(2-trifluoromethylphenyl)-1,4-dihydropyridine-3,5-dicarboxylic acid 3-[2-(4-chloro-8-methyl-3-quinolinecarboxy)ethyl]ester-5-methyl ester 6. 2,6-dimethyl-4-(2-nitrophenyl)-1,4-dihydropyridine-3,5-dicarboxylic acid 3-[2-(8-methoxy-3-quinolinecarboxy)ethyl]ester-5-methyl ester
7. 2,6-dimethyl-4-(2-trifluoromethylphenyl)-1,4-dihydropyridine-3,5-dicarboxylic acid 3-[2-(8-methoxy-3-quinolinecarboxy)ethyl]ester-5-methyl ester
8. 2,6-dimethyl-4-(2-nitrophenyl)-1,4-dihydropyridine-3,5-dicarboxylic acid 3-[2-(6-methyl-3-quinolinecarboxy)ethyl]ester-5-methyl ester
9. 2,6-dimethyl-4-(2-trifluoromethylphenyl)-1,4-dihydropyridine-3,5-dicarboxylic acid 3-[2-(6-methyl-3-quinolinecarboxy)ethyl]ester-5-methyl ester
10. 2,6-dimethyl-4-(2-nitrophenyl)-1,4-dihydropyridine-3,5-dicarboxylic acid 3-[2-(7-methoxy-3-quinolinecarboxy)ethyl]ester-5-methyl ester
11. 2,6-dimethyl-4-(2-trifluoromethylphenyl)-1,4-dihydropyridine-3,5-dicarboxylic acid 3-[2-(7-methoxy-3-quinolinecarboxy)ethyl]ester-5-methyl ester
12. 2,6-dimethyl-4-(2-nitrophenyl)-1,4-dihydropyridine-3,5-dicarboxylic acid 3-[2-(4-chloro-8-methoxy-3-quinolinecarboxy)ethyl]ester-5-methyl ester
13. 2,6-dimethyl-4-(2-trifluoromethylphenyl)-1,4-dihydropyridine-3,5-dicarboxylic acid 3-[2-(4-chloro-8-methoxy-3-quinolinecarboxy)ethyl]ester-5-methyl ester
14. 2,6-dimethyl-4-(2-nitrophenyl)-1,4-dihydropyridine-3,5-dicarboxylic acid 3-[2-(4-chloro-6-methyl-3-quinolinecarboxy)ethyl]ester-5-methyl ester
15. 2,6-dimethyl-4-(2-trifluoromethylphenyl)-1,4-dihydropyridine-3,5-dicarboxylic acid 3-[2-(5,8-dimethoxy-3-quinolinecarboxy)ethyl]ester-5-methyl ester
16. 2,6-dimethyl-4-(2-trifluoromethylphenyl)-1,4-dihydropyridine-3,5-dicarboxylic acid 3-[2-(3-(7,8-benzoquinoline)carboxy)ethyl]ester-5-methyl ester
17. 2,6-dimethyl-4-(2-trifluoromethylphenyl)-1,4-dihydropyridine-3,5-dicarboxylic acid 3-[2-(8-trifluoromethyl-3-quinolinecarboxy)ethyl]ester-5-methyl ester
18. 2,6-dimethyl-4-(2-trifluoromethylphenyl)-1,4-dihydropyridine-3,5-dicarboxylic acid 3-[2-(5,8-dimethyl-3-quinolinecarboxy)ethyl]ester-5-methyl ester
19. 2,6-dimethyl-4-(2-trifluoromethylphenyl)-1,4-dihydropyridine-3,5-dicarboxylic acid 3-[2-(8-fluoro-3-quinolinecarboxy)ethyl]ester-5-methyl ester The compounds of the present invention can be prepared by reacting a compound of the formula (II)

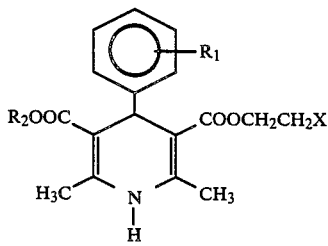

(II)

wherein $R_1$ and $R_2$ are as defined above, and X is halogen, mesyloxy, benzenesulfonyloxy, or tosyloxy with a compound of the formula (III)

(III)

wherein $R_3$ is as defined above and M is an alkali metal or an alkaline earth metal.

The reaction is preferably carried out in the presence of an inert organic solvent. Suitable solvents for the reaction include N,N-dimethylformamide, N,N-dimethylacetamide, dimethyl sulfoxide, hexamethyl phosphoamide, dioxane, acetonitrile, N-methylmorpholine, 1,2-dimethoxyethane, and the like. The reaction temperature is suitably from 80° C. to 160° C. Under the above conditions, the reaction is usually completed in a few hours.

Some of the compounds of the formula (II) are known as disclosed in, e.g., H. Meyer, E. Wehinger, F. Bossert and D. Scherling, Arzneim.-Forsch./Drug Res. 33(I), Nr. 1 (1983), and are commercially available. Also, some of the compounds of the formula (III) are commercially available.

Pharmaceutically acceptable acid addition salts of the compounds of the formula I according to the present invention may be prepared by the application or adaptation of known methods for the preparation of salts of organic bases, for example, by reacting the compounds of the formula I with the appropriate acid in a suitable solvent. Examples of addition salts include salts derived from inorganic and organic acids such as, without limitation, hydrochloric acid, phosphoric acid, sulfuric acid, acetic acid, tartaric acid, lactic acid, succinic acid, citric acid, maleic acid, sorbic acid, salicyclic acid, phthalic acid, and the like.

The new compounds may, depending on the choice of starting materials and process, be present as optical antipodes or racemate.

The racemates obtained can be separated according to known methods, e.g., by means of microorganisms, or by a reaction with optically active acids forming salts of the compound, and separating the salts thus obtained, e.g., by means of the different solubility of the diastereomeric salts, from which the antipodes may be set free by the action of a suitable agent. Suitably usable optically active acids are e.g., the L- and D-forms of tartaric acid, di-o-tolyltartaric acid, malic acid, mandelic acid, camphorsulfonic acid or quinic acid. Preferably the more active part of the two antipodes is isolated.

The compounds of the present invention have prominent inhibiting activity of calcium influx into cells as will be evident from the below-mentioned pharmacological test results, with the result of the use as vasodilator and antihypertensive agents. Thus, the compounds of the present invention can be used for treatment of a variety of diseases including cardiac diseases such as angina pectoris, arrhythmia and acute heart failure, cerebrovascular diseases such as cerebral infarction and hypertension.

In clinical use the compounds of the invention are usually administered orally, or parenterally in the form of a pharmaceutical preparation, which contains the active ingredient as free base in combination with pharmaceutically acceptable additives.

Thus the mentioning of the new compounds of the invention is here related to the free amine base even if the compounds are generally or specifically described, provided that the context in which such expressions are used, e.g., in Example 1, with this broad meaning should not correspond. The additives may be a solid, semisolid or liquid diluent or a capsule. These pharmaceutical preparations are a further object of the invention. Usually the amount of active ingredient is between 0.1 and 99% by weight of the preparation, suitably between 0.5 and 20% by weight in preparations for injection and between 2 and 50% by weight in preparations for oral administration.

In the preparation of pharmaceutical preparations containing a compound of the present invention in the form of dosage units for oral administration the compound may be mixed with a solid, pulverulent additive, e.g., with lactose, saccharose, sorbitol, mannitol, starch, such as potato starch, corn starch, amylopectin, cellulose derivatives or gelatine, as well as with a lubricant such as magnesium stearate, calcium stearate, polyethyleneglycol waxes or the like, and be pressed into tablets. If coated tablets are wanted, the above prepared core may be coated with concentrated solution of sugar, which solution may contain, e.g., gum arabicum, gelatine, talc, titanium dioxide or the like.

In the preparation of soft gelatine capsules which consist of gelatine and, e.g., glycerine, or in the preparation of similar closed capsules, the active compound is mixed with a vegetable oil. Hard gelatine capsules may contain granules of the active compound in combination with a solid, pulverulent additive such as lactose, saccharose, sorbitol, mannitol, starch (as, e.g., potato starch, corn starch or amylopectin), cellulose derivatives or gelatine.

Dosage units for rectal administration may be prepared in the form of suppositories, which contain the active ingredient in a mixture with a neutral fat base, or they may be prepared in the form of gelatine-rectal capsules which contain the active substance in a mixture with a vegetable oil or paraffin oil.

Liquid preparations for oral administration may be present in the form of syrups or suspensions, e.g., solutions containing from about 0.01% by weight to about 0.1% by weight of the active ingredient described, glycerol and propylene glycol.

The preparation of pharmaceutical tablets for peroral use is carried out in accordance with the following method:

The solid substances included are ground or sieved to a certain particle size. The binding agent is homogenized and suspended in a certain amount of solvent. The therapeutic compound and necessary auxiliary agents are mixed with continuous and constant mixing with the binding agent solution and are moistened so that the solution is uniformly divided in the mass without overmoistening any parts. The amount of solvent is usually so adapted that the mass obtains a consistency reminding of wet snow. The moistening of the pulverulent mixture with the binding agent solution causes the particles to gather together slightly to aggregates and the real granulating process is carried out in such a way that the mass is pressed through a sieve in the form of a net of stainless steel having a mesh size of about 1 mm. The mass is then placed in thin layers on a tray to be dried in a drying cabinet. This drying takes place during 10 hours and has to be standardized carefully as the damp degree of the granulate is of utmost importance for the following process and for the feature of the tablets. Drying in a fluid bed may possibly be used. In this case the mass is not put on a tray but is poured into a container having a net bottom.

After the drying step the granules are sieved so that the particle size wanted is obtained. Under certain circumstances powder has to be removed.

To the so called final mixture, disintegrating, lubricant and excipient are added. After this mixture the mass shall have its right composition for the tabletting step.

Many tablets, especially those which are rough or bitter, are coated with a coating. This means that they are coated with a layer of sugar or some other suitable coating.

The daily dose of the active ingredient varies and is dependent on the type of administration, but as a general rule it is 1 to 100 mg/day of active ingredient at peroral administration.

BEST MODE OF CARRYING OUT THE INVENTION

The following examples will serve to further typify the nature of the present invention without being a limitation on the scope thereof, the scope being defined solely by the appended claims.

EXAMPLE 1

2,6-Dimethyl-4-(2-trifluoromethylphenyl)-1,4-dihydropyridine-3,5-dicarboxylic acid 3-[2-(4-chloro-6-methyl-3-quinolinecarboxy)ethyl]ester-5-methyl ester

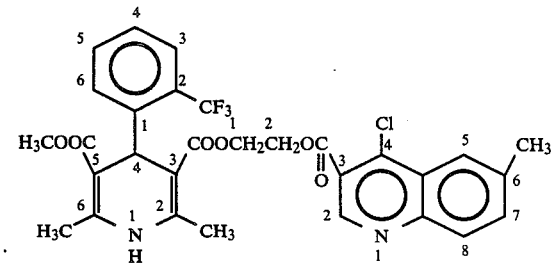

A mixture of 2,6-dimethyl-4-(2-trifluoromethylphenyl)-1,4-dihydropyridine-3,5-dicarboxylic acid 3-(2-chloroethyl)ester-5-methyl ester (1.00 g) and sodium 4-chloro-6-methyl-3-quinoline carboxylate (0.64 g) was heated and stirred in N,N-dimethyl formamide (10 ml) under an argon stream at 120°–130° C. for 4 hours. After the reaction was complete, ethylacetate (20 ml) was added to the reaction mixture, filtered with suction and the filtrate was concentrated under reduced pressure. Silicagel column chromatography of the residue eluting with ethyl acetate/n-hexane (1:1 volume ratio) gave the title compound (1.14 g, 79% yield) as non-crystalline colorless powder. This compound was measured for NMR with the following results.

$^1$H NMR (CDCl$_3$) δ 2.28 (s, 3H), 2.33 (s, 3H), 2.61 (s, 3H), 3.55 (s, 3H), 4.26–4.65 (m, 4H), 5.58 (s, 1H), 5.99 (b, 1H), 7.01–7.15 (m, 1H), 7.25–7.75 (m, 4H), 8.04 (d, 1H), 8.10–8.21 (m, 1H), 9.04 (s, 1H).

EXAMPLES 2–19

Using the appropriate starting materials and the same procedure as described in Example 1, there were prepared the compounds as shown in Table 1.

TABLE 1

Structure: 1,4-dihydropyridine with phenyl-R₁ at 4-position, $R_2OOC$ at 3-position, $COOCH_2CH_2OC(=O)-R_3$ at 5-position, 2,6-dimethyl, NH.

| Example | R₁ | R₂ | R₃ | Physical properties & Yield |
|---|---|---|---|---|
| 2 | 2-NO₂ | CH₃ | 3-methylpyridine N-oxide | Crystalline yellow powder m.p. 183–185° C., ¹H NMR (CDCl₃)δ2.31(s, 3H), 2.39 (s, 3H), 3.55(s, 3H), 4.30–4.55(m, 4H), 5.76(s, 1H), 6.07(b, 1H), 7.13–7.23(m, 1H) 7.30–7.64(m, 4H), 7.83(d, 1H), 8.33(d, 1H), 8.60(d, 1H), yield 42% |
| 3 | 2-CF₃ | CH₃ | 3-methylpyridine N-oxide | Non-crystalline colorless powder, ¹H NMR(CDCl₃)δ2.30 (s, 3H), 2.36(s, 3H), 3.57(s, 3H), 4.30–4.55(m, 4H), 5.54 (s, 1H), 5.91(b, 1H), 7.10–7.23 (m, 1H), 7.30–7.57(m, 4H), 7.78 (m, 1H), 8.33(m, 1H), 8.61(dd, 1H), yield 35% |
| 4 | 2-NO₂ | CH₃ | 4-hydroxy-3,8-dimethylquinoline | Non-crystalline yellow powder ¹H NMR(CDCl₃—CD₃OD)δ2.25 (s, 3H), 2.31(s, 3H), 2.58(s, 3H), 3.53(s, 3H), 3.60–3.90 (b, 2H), 4.25–4.55(m, 4H), 5.72 (s, 1H), 7.06–7.64(m, 5H), 7.87 (s, 1H), 8.23(d, 1H), 8.64(s, 1H), yield 45% |
| 5 | 2-CF₃ | CH₃ | 4-chloro-3,8-dimethylquinoline | Non-crystalline colorless powder, ¹H NMR(CDCl₃)δ 2.30(s, 3H), 2.35(s, 3H), 2.83(s, 3H), 3.56(s, 3H), 4.25–4.60(m, 4H), 5.58(s, 1H), 5.67(b, 1H), 7.02–7.14(m, 1H), 7.27–7.75(m, 5H), 8.27(d, 1H), 9.13(s, 1H), yield 44% |
| 6 | 2-NO₂ | CH₃ | 3-methyl-8-methoxyquinoline | Crystalline yellow powder m.p. 171–174° C., ¹H NMR(CDCl₃) δ2.30(s, 3H), 2.37(s, 3H), 3.51(s, 3H), 4.12(s, 3H), 4.35–4.64(m, 4H), 5.78(s, 1H), 5.84 (b, 1H), 6.95–7.06(m, 1H), 7.14–7.58(m, 6H), 8.75(d, 1H), 9.32 (d, 1H), yield 37% |
| 7 | 2-CF₃ | CH₃ | 3-methyl-8-methoxyquinoline | Crystalline colorless powder m.p. 197–198° C., ¹H NMR(CDCl₃) δ2.30(s, 3H), 2.34(s, 3H), 3.52(s, 3H), 4.12(s, 1H), 4.25–4.57(m, 4H), 5.56(s, 1H), 5.69 (b, 1H), 7.00–7.60(m, 7H), 8.72 (s, 1H), 9.35(s, 1H), yield 44% |
| 8 | 2-NO₂ | CH₃ | 3,7-dimethylquinoline | Non-crystalline yellow powder ¹H NMR(CDCl₃)δ2.29(s, 3H), 2.38(s, 3H), 2.58(s, 3H), 3.51 (s, 3H), 4.33–4.68(m, 4H), 5.79 (s, 1H), 6.03(b, 1H), 6.95–7.07 (m, 1H), 7.27–7.40(m, 1H), 7.40–7.60(m, 2H), 7.60–7.80(m, 2H), 8.05(d, 1H), 8.70(d, 1H), 9.23 (d, 1H), yield 46% |

TABLE 1-continued

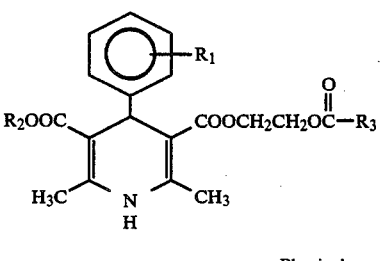

| Example | $R_1$ | $R_2$ | $R_3$ | Physical properties & Yield |
|---|---|---|---|---|
| 9 | 2-CF$_3$ | CH$_3$ | 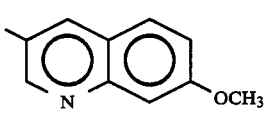 | Crystalline colorless powder m.p. 146–148° C., $^1$H NMR(CDCl$_3$) δ2.29(s, 3H), 2.34(s, 3H), 2.58(s, 3H), 3.53(s, 3H), 4.30–4.65(m, 4H), 5.57(s, 1H), 5.93 (b, 1H), 7.00–7.14(m, 1H), 7.25–7.40(m, 2H), 7.47–7.55(m, 1H), 7.60–7.73(m, 2H), 8.06(d, 1H), 8.69(d, 1H), 9.27(d, 1H), yield 69% |
| 10 | 2-NO$_2$ | CH$_3$ | 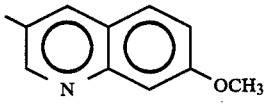 | Non-crystalline yellow powder $^1$H NMR(CDCl$_3$)δ2.29(s, 3H), 2.38(s, 3H), 3.51(s, 3H), 3.99 (s, 3H), 4.35–4.62(m, 4H), 5.79 (s, 1H), 5.88(b, 1H), 7.04(m, 1H), 7.23–7.57(m, 5H), 7.82(d, 1H), 8.68(d, 1H), 9.24(d, 1H), yield 24% |
| 11 | 2-CF$_3$ | CH$_3$ | 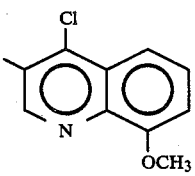 | Non-crystalline colorless powder $^1$H NMR(CDCl$_3$)δ2.29(s, 3H), 2.34(s, 3H), 3.53(s, 3H), 3.99 (s, 3H), 4.25–4.60(m, 4H), 5.58 (s, 1H), 6.01(b, 1H), 7.00–7.15 (m, 1H), 7.23–7.58(m, 5H), 7.80 (d, 1H), 8.66(d, 1H), 9.27(d, 1H), yield 34% |
| 12 | 2-NO$_2$ | CH$_3$ | 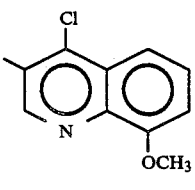 | Crystalline yellow powder m.p. 219° C.(dec.), $^1$H NMR (CDCl$_3$)δ2.30(s, 3H), 2.37(s, 3H), 3.53(s, 3H), 4.12(s, 3H), 4.36–4.65(m, 4H), 5.78(s, 2H), 6.95–7.07(m, 1H), 7.17–7.40(m, 2H), 7.43–7.56(m, 2H), 7.64(t, 1H), 7.97(d, 1H), 9.08(s, 1H), yield 48% |
| 13 | 2-CF$_3$ | CH$_3$ | 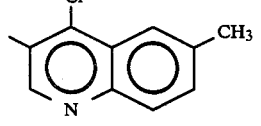 | Crystalline colorless powder m.p. 189° C. (dec.), $^1$H NMR (CDCl$_3$)δ2.30(s, 3H), 2.33 (s, 3H), 3.55(s, 3H), 4.12(s, 3H), 4.26–4.65(m, 4H), 5.58 (s, 1H), 5.84(b, 1H), 7.02–7.16 (m, 1H), 7.16–7.56(m, 1H), 7.64 (t, 1H), 7.98(d, 1H), 9.11(s, 1H), yield 60% |
| 14 | 2-NO$_2$ | CH$_3$ | 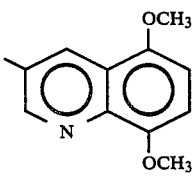 | Non-crystalline yellow powder $^1$H NMR(CDCl$_3$)δ2.30(s, 3H), 2.39(s, 3H), 2.62(s, 3H), 3.54 (s, 3H), 4.36–4.63(m, 4H), 5.79 (s, 1H), 5.87(b, 1H), 6.95–7.06 (m, 1H), 7.26–7.40(m, 1H), 7.40–7.56(m, 2H), 7.64–7.75(m, 1H), 8.04(d, 1H), 8.13–8.20(m, 1H), 9.02(s, 1H), yield 46% |
| 15 | 2-CF$_3$ | CH$_3$ | | Crystalline pale greenish blue powder, $^1$H NMR(CDCl$_3$)δ2.29 (s, 3H), 2.32(s, 3H), 3.51(s, 3H), 4.00(s, 3H), 4.06(s, 3H), 4.28–4.56(m, 4H), 5.55(s, 1H), 5.87 (s, 1H), 6.83(d, 1H), 7.00–7.12 (m, 1H), 7.08(d, 1H), 7.25–7.53 (m, 3H), 9.16(d, 1H), 9.36(d, 1H), yield 85% |

TABLE 1-continued

| Example | R₁ | R₂ | R₃ | Physical properties & Yield |
|---|---|---|---|---|
| 16 | 2-CF₃ | CH₃ | (3-methyl-benzo[f]quinolinyl) | Non-crystalline colorless powder, ¹H NMR(CDCl₃)δ 2.28(s, 3H), 2.34(s, 3H), 3.53(s, 3H), 4.30–4.65(m, 4H), 5.58(s, 1H), 5.82(b, 1H), 7.00–7.13(m, 1H), 7.23–7.54(m, 4H), 7.65–8.00(m, 4H), 8.73(d, 1H), 9.24–9.35(m, 1H), 9.43(d, 1H), yield 85% |
| 17 | 2-CF₃ | CH₃ | (3-methyl-8-trifluoromethyl-quinolinyl) | Non-crystalline colorless powder ¹H NMR(CDCl₃)δ2.28(s, 3H), 2.34(s, 3H), 3.53(s, 3H), 4.27–4.67(m, 4H), 5.57(s, 1H), 5.88 (b, 1H), 7.02–7.15(m, 1H), 7.25–7.44(m, 2H), 7.45–7.56(m, 1H), 7.63–7.76(m, 1H), 8.07–8.26(m, 2H), 8.83(d, 1H), 9.45(d, 1H), yield 81% |
| 18 | 2-CF₃ | CH₃ | (3,4,8-trimethyl-quinolinyl) | Non-crystalline colorless powder ¹H NMR(CDCl₃)δ2.30(s, 3H), 2.34(s, 3H), 2.70(s, 3H), 2.79 (s, 3H), 3.52(s, 3H), 4.27–4.60 (m, 4H), 5.58(s, 1H), 5.71(b, 1H), 7.02–7.12(m, 1H), 7.24–7.58(m, 5H), 8.93(d, 1H), 9.37(d, 1H), yield 71% |
| 19 | 2-CF₃ | CH₃ | (3-methyl-8-fluoro-quinolinyl) | Non-crystalline colorless powder, ¹H NMR(CDCl₃)δ 2.30(s, 3H), 2.35(s, 3H), 3.53(s, 3H), 4.30–4.58(m, 4H), 5.53–5.57(m, 1H), 5.73(b, 1H), 7.01–7.13(m, 1H), 7.25–7.80 (m, 6H), 8.80(dd, 1H), 9.38(d, 1H), yield 80% |

The novel compounds as prepared in the above-mentioned examples were individually measured for Ca-blocking potency thereof in accordance with the method of M. Fiol de Cureo et al. (Arch. int. Pharmacodyn., 263, 28–39, 1983). This method is to evaluate each compound to be tested with respect to Ca-blocking potency on the basis of 50% inhibiting concentration of a spontaneous contraction of an isolated rat portal vein. The results are shown in terms of a relative activity to Nifedipine (Nifedipine=1) in Table 2.

TABLE 2

Ca-blocking potency of 1,4-dihydropyridine derivatives

| Example | R₁ | R₂ | R₃ | Specific potency |
|---|---|---|---|---|
| 1 | 2-CF₃ | CH₃ | (4-chloro-3,6-dimethyl-quinolinyl) | 21.7 |
| 2 | 2-NO₂ | CH₃ | (3-methyl-pyridinyl N-oxide) | 5.9 |
| 3 | 2-CF₃ | CH₃ | (3-methyl-pyridinyl N-oxide) | 9.0 |

TABLE 2-continued
Ca-blocking potency of 1,4-dihydropyridine derivatives

| Example | R₁ | R₂ | R₃ | Specific potency |
|---|---|---|---|---|
| 5 | 2-CF₃ | CH₃ | 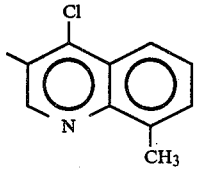 | 3.1 |
| 6 | 2-NO₂ | CH₃ | 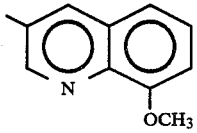 | 1.9 |
| 7 | 2-CF₃ | CH₃ | 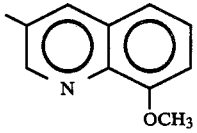 | 3.6 |
| 8 | 2-NO₂ | CH₃ | 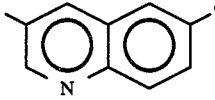 | 10.8 |
| 9 | 2-CF₃ | CH₃ | 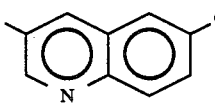 | 9.6 |
| 10 | 2-NO₂ | CH₃ | 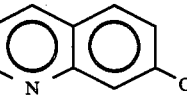 | 3.6 |
| 11 | 2-CF₃ | CH₃ | 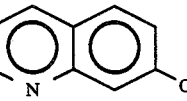 | 8.8 |
| 13 | 2-CF₃ | CH₃ | 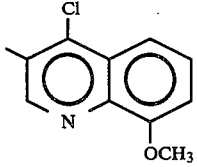 | 1.8 |
| 14 | 2-NO₂ | CH₃ | 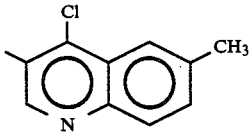 | 28.3 |
| 15 | 2-CF₃ | CH₃ | 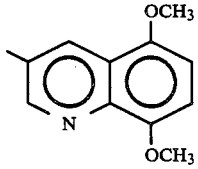 | 5.4 |
| 16 | 2-CF₃ | CH₃ | 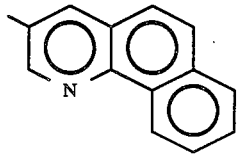 | 9.7 |
| 17 | 2-CF₃ | CH₃ | 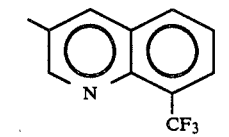 | 5.0 |
| 18 | 2-CF₃ | CH₃ | 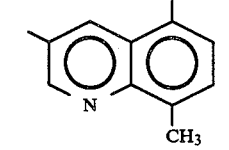 | 2.4 |
| 19 | 2-CF₃ | CH₃ | 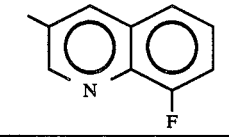 | 6.9 |

EXAMPLE 20

A syrup containing 0.5% (weight per volume) of active ingredient was prepared from the following ingredients:

| | |
|---|---|
| Active ingredient | 0.5 g |
| D-sorbitol 70 W/V % | 25 g |
| Sugar | 30 g |
| Methyl p-oxybenzoate | 0.03 g |
| Glycerine | 0.15 g |
| Propyl p-oxybenzoate | 0.015 g |
| Flavoring agent | 0.2 g |
| 96% Ethanol | 0.5 g |
| Distilled water | ad 100.0 ml |

Sugar, d-sorbitol and the active ingredient were dissolved in 60 g of warm water. After cooling, glycerine and a solution of flavoring agents dissolved in ethanol were added. To the mixture water was then added to 100 ml.

The above named active ingredient may be replaced by other therapeutically active ingredients of the invention.

EXAMPLE 21

An active ingredient (50 mg) was mixed with lactose (50 mg), potato starch (20 mg) and colloidal silicic acid (9.5 mg). The mixture was moistened with a 10% solution of gelatine and was granulated through a 12-mesh sieve. After drying potato starch (10 mg), talc (0.75 mg) and magnesium stearate (0.75 mg) were admixed and the mixture thus obtained was pressed into tablets, each containing 50 mg of active ingredient. These tablets are coated with a 10% alcoholic solution of shellac and thereupon with an aqueous solution containing saccharose (45%), gum arabicum (5%), gelatine (4%) and dyestuff (0.2%). After the first five coatings talc and powdered sugar were used for powdering. The priming coat was then coated with a 66% sugar syrup and polished with a 10% carnauba wax solution in carbon tetrachloride.

EXAMPLE 22

Granules were prepared from active ingredient (50 mg), lactose (250 mg), potato starch (150 mg) and an alcoholic solution of polyvinylpyrrolidone (50 mg). After the drying step the granules were sieved through a 12×60 mesh sieve to prepare granules, each containing 50 mg of active ingredient.

What is claimed is:

1. A compound of formula I

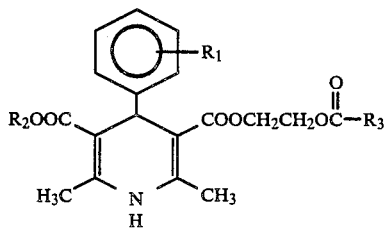

wherein $R_1$ is a nitro or trifluoromethyl group; $R_2$ is a $C_1-C_6$ alkyl group; $R_3$ is a pyridyl or pyridyl N-oxide group fused with a benzene or naphthalene ring, said ring being optionally substituted with $C_1-C_6$ alkyl, $C_1-C_6$ alkoxy, halogen or haloalkyl wherein the alkyl moiety has 1-3 carbon atoms, said pyridyl or pyridyl N-oxide group optionally being substituted at a carbon atom with halogen or hydroxyl, and a pharmaceutically acceptable acid addition salt thereof.

2. A compound of claim 1 wherein $R_1$ is 2-nitro, 3-nitro, 2-trifluoromethyl or 3-trifluoromethyl.

3. A compound of claim 1 wherein $R_2$ is $C_1-C_4$ alkyl.

4. A compound of claim 1 wherein $R_3$ is a pyridyl N-oxide group fused to said benzene or nagphthalene ring.

5. A compound of claim 1 wherein $R_3$ is a pyridyl group fused to said benzene or naphthalene ring, said pyridyl group optionally being substituted at a carbon atom with halogen or hydroxyl and said benzene or naphtnalene ring optionally being substituted with one or more of $C_1-C_6$ alkyl, $C_1-C_6$ alkoxy, halogen or haloalkyl wherein the alkyl moiety has 1-3 carbon atoms.

6. A pharmaceutical composition useful as a vasodilating or antihypertensive agent which comprises a therapeutically effective amount of a compound of claim 1 or pharmaceutically acceptable addition salts thereof, optionally in admixture with additives for a pharmaceutical preparation.

7. A pharmaceutical composition useful as a vaodilating or antihypertensive agent which comprises a therapeutically effective amount of a compound of claim 2 or pharmaceutically acceptable addition salts thereof, optionally in admixture with additives for a pharmaceutical preparation.

8. A pharmaceutical composition useful as a vasodilating or antihypertensive agent which comprises a therapeutically effective amount of a compound of claim 3 or pharmaceutically acceptable addition salts thereof, optionally in admixture with additives for a pharmaceutical preparation.

9. A pharmaceutical composition useful as a vasodilating or antihypertensive agent which comprises a therapeutically effective amount of a compound of claim 4 or pharmaceutically acceptable addition salts thereof, optionally in admixture with additives for a pharmaceutical preparation.

10. A pharmaceutical composition useful as a vasodilating or antihypertensive agent which comprises a therapeutically effective amount of a compound of claim 5 or pharmaceutically acceptable addition salts thereof, optionally in admixture with additives for a pharmaceutical preparation.

* * * * *